(12) United States Patent
Hartung

(10) Patent No.: US 7,745,107 B2
(45) Date of Patent: Jun. 29, 2010

(54) METHOD FOR ASSAYING FLOWING MEDIA FOR MICROBIAL TOXINS

(76) Inventor: Thomas Hartung, Kanzleistrasse 28, DE-78462, Konstanz (DE)

( * ) Notice: Subject to any disclaimer, the term of this patent is extended or adjusted under 35 U.S.C. 154(b) by 811 days.

(21) Appl. No.: 10/474,694

(22) PCT Filed: Mar. 25, 2002

(86) PCT No.: PCT/DE02/01086

§ 371 (c)(1),
(2), (4) Date: Apr. 7, 2004

(87) PCT Pub. No.: WO02/084295

PCT Pub. Date: Oct. 24, 2002

(65) Prior Publication Data

US 2004/0161766 A1 Aug. 19, 2004

(30) Foreign Application Priority Data

Apr. 12, 2001 (DE) ............................... 101 18 446

(51) Int. Cl.
*C12Q 1/68* (2006.01)
(52) U.S. Cl. ............................. 435/4; 435/7.2; 435/6; 210/321.79; 210/690
(58) Field of Classification Search .................... None
See application file for complete search history.

(56) References Cited

U.S. PATENT DOCUMENTS

| | | | |
|---|---|---|---|
| 4,436,620 A * | 3/1984 | Bellotti et al. ................ 210/90 |
| 4,816,162 A * | 3/1989 | Rosskopf et al. ............ 210/651 |
| 5,403,917 A * | 4/1995 | Boos et al. ................... 530/351 |
| 5,605,627 A * | 2/1997 | Carlsen et al. .......... 210/321.79 |
| 5,626,760 A * | 5/1997 | Pouchoulin ................. 210/645 |
| 5,679,775 A * | 10/1997 | Boos et al. ................... 530/351 |
| 5,855,782 A * | 1/1999 | Falkenhagen et al. ..... 210/323.1 |
| 5,891,728 A * | 4/1999 | Wendel et al. .................. 436/2 |
| 5,981,294 A * | 11/1999 | Blatt et al. ................... 436/178 |
| 6,251,873 B1 * | 6/2001 | Furusako et al. .............. 514/44 |
| 6,409,699 B1 * | 6/2002 | Ash ............................ 604/29 |
| 6,461,517 B1 * | 10/2002 | Miwa et al. ................. 210/690 |
| 6,468,734 B2 * | 10/2002 | Kobayashi et al. ............. 435/4 |
| 6,627,426 B2 * | 9/2003 | Biddle et al. ................ 435/243 |
| 6,692,696 B1 * | 2/2004 | Alberte ........................ 422/50 |
| 6,881,408 B1 * | 4/2005 | Heinrich et al. .......... 424/140.1 |
| 2001/0006791 A1 * | 7/2001 | Kobayashi et al. ......... 435/7.21 |

(Continued)

FOREIGN PATENT DOCUMENTS

EP 0743084 * 11/1996

(Continued)

OTHER PUBLICATIONS

Fennrich et al (1999) reference of record.*

(Continued)

*Primary Examiner*—Robert B Mondesi
*Assistant Examiner*—Ginny Portner
(74) *Attorney, Agent, or Firm*—The Nath Law Group; Joshua B. Goldberg; Tanya E. Harkins

(57) ABSTRACT

Testing of flowing media for microbial toxins via whole blood incubation in a flow vessel containing a separation element and assaying for mediators.

9 Claims, 3 Drawing Sheets

U.S. PATENT DOCUMENTS

Figure 1:
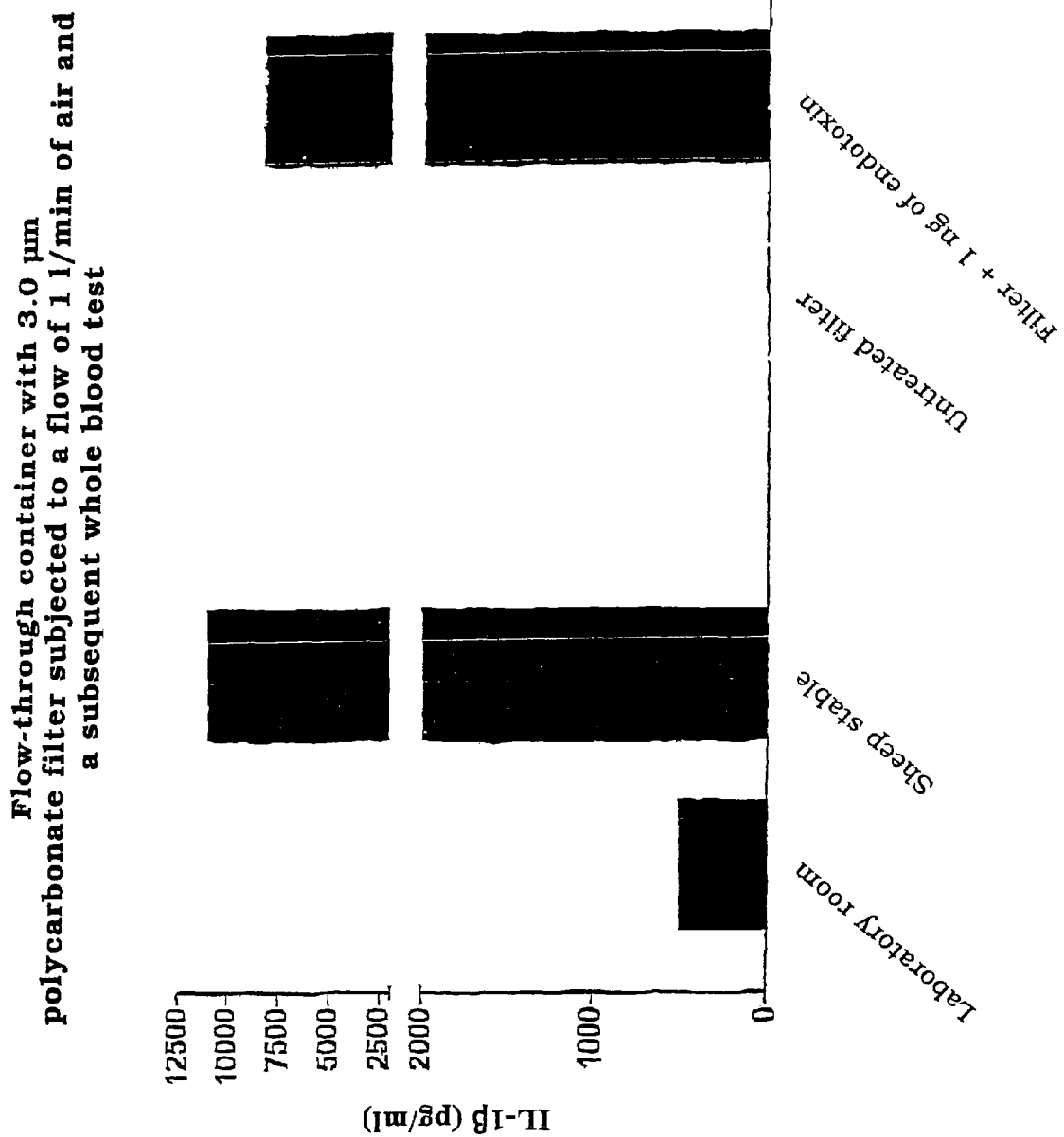

| | | | |
|---|---|---|---|
| 2001/0014443 A1* | 8/2001 | Kobayashi et al. | 435/4 |
| 2002/0146412 A1* | 10/2002 | Brady et al. | 424/140.1 |
| 2002/0146413 A1* | 10/2002 | Brady et al. | 424/140.1 |
| 2002/0190000 A1* | 12/2002 | Baurmeister | 210/650 |
| 2003/0080056 A1* | 5/2003 | Boos et al. | 210/634 |
| 2003/0130194 A1* | 7/2003 | Altrichter et al. | 514/12 |
| 2003/0216677 A1* | 11/2003 | Pan et al. | 604/5.04 |
| 2004/0228837 A1* | 11/2004 | Chen et al. | 424/85.2 |
| 2005/0009001 A1* | 1/2005 | Seidel et al. | 435/2 |
| 2005/0014678 A1* | 1/2005 | Lowe et al. | 514/2 |
| 2005/0029193 A1* | 2/2005 | Matson | 210/645 |
| 2005/0090020 A1* | 4/2005 | Wendel et al. | 436/518 |
| 2005/0169942 A1* | 8/2005 | Li et al. | 424/239.1 |
| 2005/0281809 A1* | 12/2005 | Roberts et al. | 424/140.1 |

FOREIGN PATENT DOCUMENTS

| | | | |
|---|---|---|---|
| EP | 0787500 A1 * | 6/1997 | |
| EP | 0 851 231 A1 | 7/1998 | |
| EP | 0958839 | * | 11/1999 |
| JP | 0037172 | * | 6/2000 |
| WO | 0067900 | * | 11/2000 |

OTHER PUBLICATIONS

Fennrich et at (1999) reference of record.*
Altex, Jan. 18, 2001, reference of record, sited by Applicant.*
Lonneman, Gerhard, Nephrol. Dial. Transplant., 1998, vol. 13, (Suppl. 5, 17-20), Assessment of the quality of dialysate.*
Fennrich, S., et al. "A new application for the human whole blood tes: development of an assay to assess the health risk of air-borne microbial contaminantions!", *Altex, Alternativen Zu* Tierrexperimenten, Bd. 18, Nr. 1, pp. 41-46, (2001).
Fennrich, S., et al., "Detection of Endotoxins and other Pyrogens Using Human Whole Blood", *Developments in Biological* Standardization, Bd. 101, pp. 131-139 (1999).
Case, G.D., et al., "Interactions of Blood Metalloproteins with Nitrogen Oxides and Oxidant Air Pollutants", *Environmental Research* v. 20, pp. 43-65, (1979).

* cited by examiner

METHOD FOR ASSAYING FLOWING MEDIA FOR MICROBIAL TOXINS

The health of living beings depends essentially among other things on the air quality of the direct living environment. The quality of the room air conditions, such as in living space and work rooms, factory buildings, public buildings and transportation, in rooms without air conditioning but especially in rooms with air conditioning, is chiefly determined by the components temperature, humidity and the content of dust and immune-activating pollutants in the air. Contamination with environmental germs, e.g. with microorganisms such as mold and bacteria, with their toxins and decay products, e.g. with endotoxins of Gram-negative bacteria or their equivalents in Gram-positive bacteria, play a central role here. Such pollutants of the inside air could represent a causative factor for "sick-building syndrome" with the symptoms of a feeling of sickness, concentration weakness, headaches, mucous-membrane irritation and a dry-air feeling up to breathing difficulty, a feeling of thoracic constriction and increased susceptibility to allergies and infection. Millions of people employed in air-conditioned rooms suffer from these symptoms.

In living quarters, persistent moisture in or on construction materials is the main cause of microbial contamination with bacteria and mold. This problem is increased even more by the trend towards sealing buildings to a greater extent for the purpose of saving energy and by the collection of organic waste. It is foreseeable that microbial pollutants will further increase in the future in living and working areas as a cause of health problems. Forced ventilation of living areas, working areas and public buildings with air conditioners, which can be colonized by microbial germs and spread their toxins, increases the danger. In work areas, polluted work environments have also been found, for example, in hospitals, in industrial companies as in the steel industry, in printing shops, in pet shops, animal pens, zoos, chicken farms or waste-sorting plants.

Liquids such as water, aqueous solutions, biological liquids, but also technical liquids, above all liquids and their vapors that come into contact or are in contact with the human body, can also be contaminated with cell-activating components such as pyrogens, with substantial consequences in part for products manufactured from them. Among these are, for example, drinks, infusion or injection solutions, sera, dialysis liquids, disinfectants, e.g. for the cleaning of medical materials, rinsing solutions for commercial use and use in medicine, e.g. for rinsing out the abdominal cavity, the hollow spaces of organs during operations or the lung to obtain bronchial lavage, liquid additives in air-conditioning systems for humidification or liquid mixtures for cooling hot materials during processing, e.g. in the steel industry. Life-preservation systems that maintain themselves are playing an increasingly greater role in modern technology, for example gases, such as breathable air, and liquids, such as water, in space travel or diving technology.

Attempts at contamination evaluation of filter materials or air filters loaded with endotoxins and then dried did not prove reliably reproducible. In the case of liquids, there are also problems with the frequently very low concentrations of occasionally very small toxin contaminants and the presence of interfering substances. The methods and evaluation criteria for the detection, characterization and quantification of the contamination levels have proven on the whole to be unsatisfactory and urgently in need of improvement. A dependable assaying method that is simple and leads to clear and reproducible results is lacking.

BRIEF DESCRIPTION OF THE DRAWINGS

FIG. 1: Shows the quantification and comparison of interleukin-1β measured by whole blood test utilizing a flow-through container with a 3.0 μm polycarbonate filter subjected to a flow of 1 liter/minute of air relative to a control untreated filter.

FIG. 2: Shows whole blood incubation of the flow-through container with polyethylene styrene filters after the filtration of various volumes of solution containing endotoxin relative to a control sample.

FIG. 3: Shows a flow-through or collection container (1) with a cylindrical casing (2) containing a separation element (3) and covers at the supply opening (4) and the outlet opening (5), the covers being impermeable to toxins and provide for closure of the container.

This problem is solved in accordance with the invention by a method for testing and, if applicable, quantitatively assaying gases and liquids for their content of microbiological toxins using a separation method, wherein separation elements that are contained in a flow-through container are used to separate microbiological toxins from the gas or the liquid, the flow-through container with separation elements is used as an incubation vessel for incubation with immune-reactive cells, as with the whole-blood detection method, after the gas or the liquid to be tested flows through, and then an assay for mediators formed during the incubation phase in the presence of toxins is carried out after the incubation in a way that is known in and of itself.

Gases as defined by the invention are gaseous, flowing media of all types. Particular examples of these are air, e.g. from living and working areas, for which reference is made to the remarks above, but also aerosols such as dust and mist. Other examples of gases and gas mixtures that can be tested according to the method in accordance with the invention are anesthetic gases, protective gases or gases that are inert with regard to reaction and protective-gas mixtures, e.g. for industrial, biotechnological, pharmaceutical and food-related processes, such as fermentation, cell cultures and the like, carbon dioxide, nitrogen and their mixtures with other gases. Generally fluid media, especially with low and medium viscosity, Newtonian liquids and sols are among the examples of liquids as defined by the invention. Water, e.g. for and from the drinking-water treatment system, aqueous solutions, emulsions, dispersions and suspensions are very much preferred. Biological liquids such as urine, blood, liquid blood components, such as serum or plasma, and blood replacement products, for example, are among the liquids that can be tested. Reference is also made with regard to this, to avoid repetition, to the examples of liquids mentioned at the outset, above all from the food-related, medical and technological sectors.

Endotoxins, pyrogens, microbial contaminations in general, immune-activating or cell-activating substances and components, including biological weapons, above all synthetic warfare agents, as well as substances, components and particles that form materials of the above-mentioned type or that are capable of releasing them, for example, are among the microbiological toxins as defined by the invention.

Any inert materials and devices that are capable of absorbing and retaining, and thus separating, microbiological toxins from the respective testing medium, gas or liquid, if any are even contained in it, or at least contained in relevant amounts, to an extent sufficient for detection, while gases and liquids are essentially able to pass through, can be used as separation elements. The designations of gases and liquids do not necessarily, although it is a preference, refer to the aggregate state at room temperature, but instead to the aggregate state during the separation. Any separation elements, for example, that are capable of separating out microbiological toxins from the flowing medium that is brought into contact with it via sorption, above all adsorption, but also absorption, via a reaction with the toxin and/or in a mechanical sense, e.g. via screen filtration or deposition on the surface of the separation element, are suitable. The separation can be done in a quantitative fashion, e.g. with regard to freeing gases and liquids of toxins, but especially with regard to the quantitative determination of the toxin contamination in the respective test medium.

The invention also involves the separation of toxins in a quantity required for their qualitative detection, though. Separation elements that are very much preferred are filters, also those in the customary sense, such as filter paper, filter pads or filter fleeces made of the most diverse materials, such as filters containing fibers made of cellulose or cellulose esters, PVC, polyesters, polycarbonates or polytetrafluoroethylene. Inorganic filter materials, e.g. with fiberglass as a filter material, as well as glass and porcelain frit, could be used in addition to, or in place of, separation elements based on organic filter materials. Furthermore, polar, non-polar, organic, inorganic, porous or microporous granules such as ion-exchange resins, as well as diatomite, perlite, active charcoal, melamine resin, proteins and/or polyamide, are also suitable as separation elements, also arranged on carriers. As a preference, the separation elements will particularly have porous granules such as ion-exchange resins or toxin-reactive groups or charging. This permits the choice of a special adaptation to the test medium and to the toxin type and amount expected. When gases such as air are used as test medium, filter papers or filter pads, for example, have particularly proven themselves for reasons relating to the flow (filtrate speed), whereas granules with a suitable pore size and layer thickness of an ion-exchange displaying toxin-reactive groups or other separation elements of the above-mentioned type with toxin-reactive groups have especially proven themselves as separation elements to separate toxins from a liquid test medium such as blood or blood components. Molecular sieves can also be used in extreme cases. Microfiltration as it is used with the familiar filters for the separation of proteins, pyrogens, enzymes and viruses and for the manufacture of germ-free products is also suitable, or even ultrafiltration with membrane filters, e.g. with pore sizes of 0.2 µm to 20 µm. Pressure filtration may be used to set the desired ratios of filtrate speed and separation efficiency. Typical filters could have pore sizes, for example, of 1 to 10 µm, in particular 3 to 8 µm, depending on the viscosity of the medium to be tested and the type and quantity of the toxin that is expected. In the case of liquids, filters with larger pores have also proven themselves in part; the particle size of the expected toxins must also be taken into consideration in each case.

The separation elements are put into flow-through containers in a removable or non-removable form. In the case of separation elements that are connected with the flow-through containers in a removable form, arrangement of the separation elements as insets in a frame, e.g. made of polystyrene, has proven itself.

The use of insets of this type has the advantage of multiple reusability of a flow-through container thanks to the exchangeability of the inset. Thus, air collection devices according to EN, DIN or ISO standards-can be used, for example. The arrangement of removable granules with toxin-reactive groups in the form of an ion-exchange resin in accordance with the invention has proven to be particularly advantageous when liquid media such as blood or blood components are used, because these can then be taken from the flow-through device for incubation in an incubation vessel and, if applicable, regeneration after any exhaustion of the binding capacity of the filter cake. The flow-through container itself is usually made from an inert material such as plastic or metal in a pipe, funnel or box form with oval, rectangular, circular, polygonal cross sections or even any other arbitrary cross section as needed; the size of the cross-sectional surface in the area of the separation elements is above all determined by the viscosity of the test medium, the expected throughput amount, the predetermined throughput speed (filtration speed), the expected type and possible concentration of the toxins, whether in the main or side stream, and the like. The filtration speed and volume of the gas or liquid flow can be predetermined according to the principle of pressure filtration by pumping or sucking it through and in the case of liquids, for example, by the flow-through container using the force of gravity dependent on the cross-sectional area and the thickness of the layer or filter-cake of the separation element. Thus, in the case of a toxin concentration that is beneath the detection limit in the flowing medium or an extremely low toxin concentration, enrichment makes the detection of toxins possible or ensures reliable detection. The concentration of microbiological toxins in the test medium, e.g. in the blood or serum, can be determined by quantitative separation of the toxins, e.g. via micro- or ultrafiltration or via separation elements with toxin-reactive groups, by measuring the flow volume. This can also be used to determine the actual contaminatory burden on a person based on the average respiratory volume of 6-18 liters of air/min of an adult. 2-chamber collection tanks with their two chambers separated by a separation element, for example, are also understood to be flow-through containers in the sense that is meant here. They can above all be used for testing liquids after one chamber is loaded, making use of gravity (centrifuging), for example, as a flow aid. The subject matter of this method is accordingly also a flow-through container with at least two openings, a supply opening to bring in the flowing medium to be tested and an outlet opening, as well as associated removable or non-removable separation elements for separating out microbiological toxins; the separation element is located in the flow area between the supply opening and the outlet opening.

As a preference, the separation element, also in the form of a filter cake, is arranged so as to be essentially perpendicular to the main direction of flow and/or arranged in such a way that a forced flow is achieved through the separation element, e.g. via an extension of the separation element essentially over the entire cross-sectional area of the flow-through container in the area of the location of the separation element. In a preferred design, the flow-through container has sealing elements in the respective opening area (supply opening, outlet opening) that ensure closure, e.g. with caps or similar cover locks, impermeable to toxins. Covers with seal elements, if necessary, and adapted to the openings are provided to seal the openings.

A particular advantage lies in the fact that the incubation with immune-reactive cells, or according to the whole blood detection method, can be carried out in the flow-through container that contains the separation element as the carrier of any microbiological toxins from the flowing medium without hereby ruling out, for example, the whole-blood incubation of the separation element in a separate incubation vessel after the removal of the separation element from the flow-through device when a blood serum or plasma is used as the test liquid and toxin-reactive granules are used as the separation elements. On the one hand, the initial method mentioned is especially simple and rules out any falsification or artifacts caused by handling, such as the removal, or the transfer and transport of the separation element for further investigation. Aside from the fact that the incubation can be carried out immediately without separation measures, and thus right on site, this method has the advantage, on the other hand, that a flow-through container of this type can be sent after simple sealing, e.g. with the covers provided for that purpose, without further ado to specialized laboratories for determination of microbiological toxins according to the immune-reactive, whole blood incubation method. The method in accordance with the invention leads simply and reliably to clear, reproducible results.

Whole blood detection methods or incubation methods are understood in the present context to mean methods that are described in EP 0 741 294 A2 and/or EP 0 851 231 A2 and that are part of the content of the explanations here through this express reference.

In accordance with the invention, the separation elements of the flow-through containers are brought into contact under incubation with preparations containing whole blood after the flowing medium has passed through to determine microbiological toxins. The preparation is then investigated after incubation in a way that is familiar in and of itself, e.g. in ELISA or EIA, for the formation of mediators, e.g. cytokines such as IL-1, IL-6, TNF, prostaglandin $E_2$.

Animal or human whole blood such as freshly-obtained, possibly diluted blood of healthy donors, for example, can be used as a reagent without separation of individual components in the process. The leukocytes thus remain in their natural composition and environment. At the same time, all of the serum components that could have an influence on the effect of a toxin are present. The whole blood contains coagulation-delaying or anticoagulation components such as citrate, e.g. in a final concentration of 0.38%, or heparin, such as Na-heparin or heparin fractions; the understanding essentially is here that the coagulation-delaying or anticoagulation components also do not interfere with the incubation reaction or even go so far as to falsify it. A dilution of the whole-blood preparation, e.g. with isotonic solutions or with cell-culture medium, for example RPMI 1640, or for example a 20% dilution with a physiological saline solution, is advantageous. As a precaution, antibiotics such as penicillin or streptomycin can be added without disturbing the reaction. The incubation is carried out at increased temperatures, preferably in the range of 35 to 38° C. over a period of approx. 2 to 24 hours. When carrying out the whole blood detection, work should be done under exclusion of relevant contaminations of the device and reagents.

The method is highly sensitive and independent of the donor to a great extent (a few pg/ml of toxins lead to the release of mediators such as cytokines). Preparations of Gram-negative and Gram-positive bacterial walls such as endotoxin and lipoteichoic acid can be used for the positive control; a pyrogen-free, physiological saline solution, for example, can be used for the negative control.

The method has a whole series of advantages. The body's own primary reaction of forming mediators in response to microbiological toxins is used for the investigation. All of the blood components that may be necessary for an interaction of the toxins with the leukocytes are present, e.g. the LPS-binding protein LBP, the bactericidal permeability-increasing protein BPI, soluble CD 14, defensins, etc. The whole blood detection or incubation can incidentally also be carried out with the whole blood of the affected party with a flowing test medium, gas or liquid, from this party's individual surroundings. The individual reaction capability can be determined in this way, and a hypersensitive patient can be identified.

The use of deep-frozen blood or collectives of deep-frozen blood in the form of standardized blood unit doses has proven itself for series tests or comparison tests over certain time periods for reasons of standardization (EP 0 951 231 A2). The measures explained there form part of the explanations here.

To carry out the method in accordance with the invention, work can be done, for example, with whole blood preparations made up of 8 ml of physiological saline solution of clinical quality and 2 ml of heparinized whole blood (taken with 7.5 ml heparinized monovettes from the company Sarstedt) from healthy donors. The flow-through containers loaded with the whole blood preparation are incubated in the incubator, e.g. at 37° C., 5% $CO_2$ over night (18-24 hours). The incubated solution can then be remixed well with a pipette, transferred into a sterile falcon tube and, for example, centrifuged for 2 minutes at 4000 g and room temperature. The supernatants can be stored in the cold, then measured in an ELISA for interleukin-1β and quantified optically (OD), then converted into the quantity of interleukin-1 (IL-1) by means of a standard that is carried through. Flow-through containers with untreated filters serve as the control (FIG. 1).

EXAMPLE 1

The air of a sheep stable or of a laboratory room was drawn through flow-through containers containing a polycarbonate filter with a diameter of 12 mm as a separation element for one hour with 1 l of air per minute. A comparison was done with an untreated filter and a filter to which 1 ng of endotoxin had been applied. The whole blood incubation of the separation element was done with 400 μl of clinical saline and 50 μl of heparinized blood of a healthy donor over night. The quantity of interleukin-1β that was released was quantified in an ELISA using a recombinant standard (FIG. 1).

EXAMPLE 2

Figure 2:
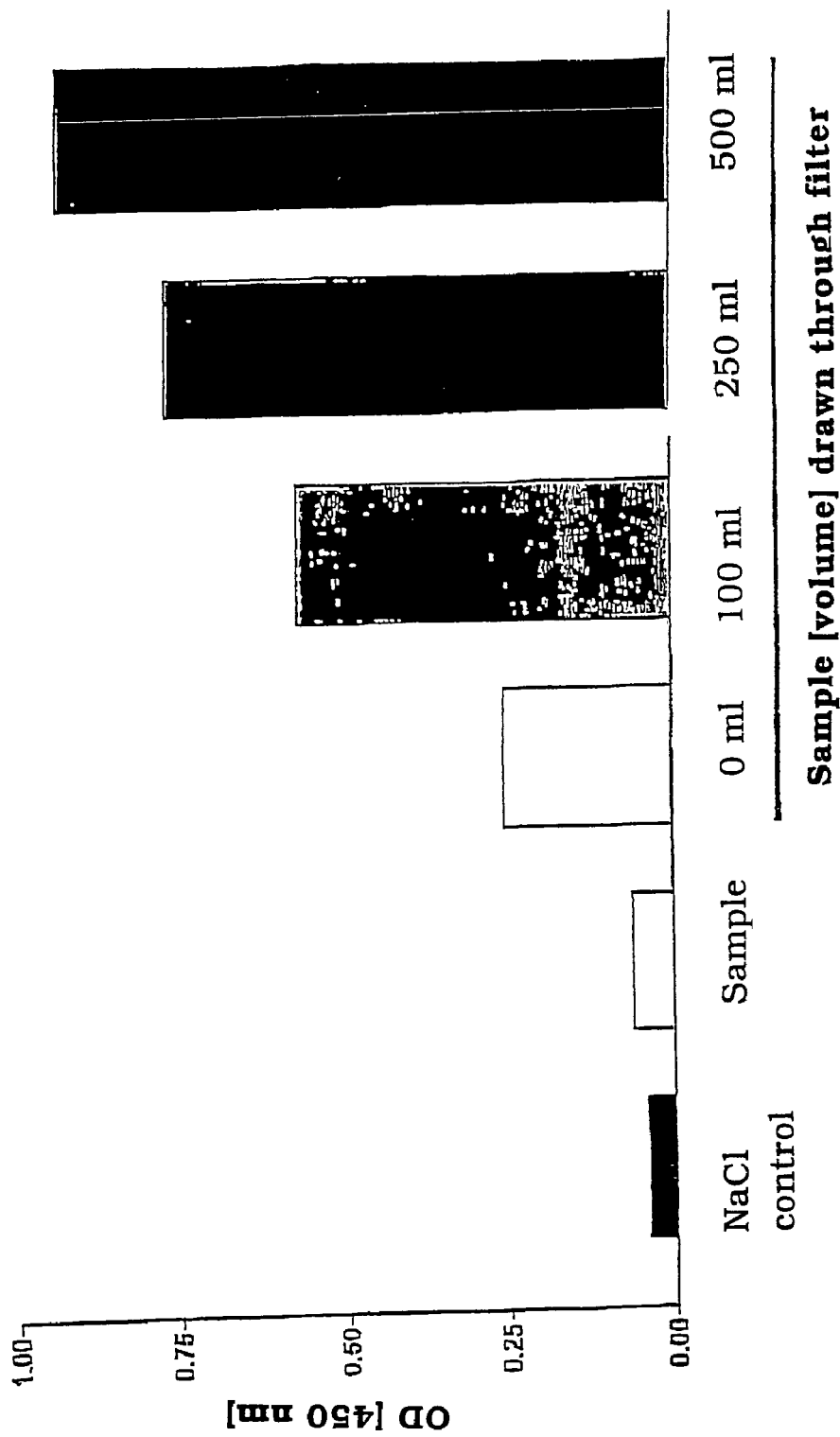

A saline solution to which 10 pg/ml of endotoxin from *E. coli* was added was used to test liquids. The sample was diluted in a ratio of 1:10 to a contamination concentration below the detection limit. A polycarbonate flow-through container with a polyethylene styrene filter with a pore diameter of 0.2 μm was used for separation. The solution to be tested was sucked through the filter by creation of a vacuum (filtration volume 100 ml, 250 ml or 500 ml). The flow-through containers with filters were incubated for 24 h at 37° C., 5% $CO_2$, after the addition of 400 μl of physiological (clinical) saline solution and 50 μl of heparinized blood, and IL-1β was identified in ELISA in the supernatant. FIG. 2 shows that the sample with the low endotoxin contamination provides a signal similar to the saline control. The flow-through container with the untreated filter itself gives a low signal (0 ml) that is increased depending on the sample quantity that is run through. A quantifiable amount of endotoxin was therefore retained and enriched.

Figure 3:
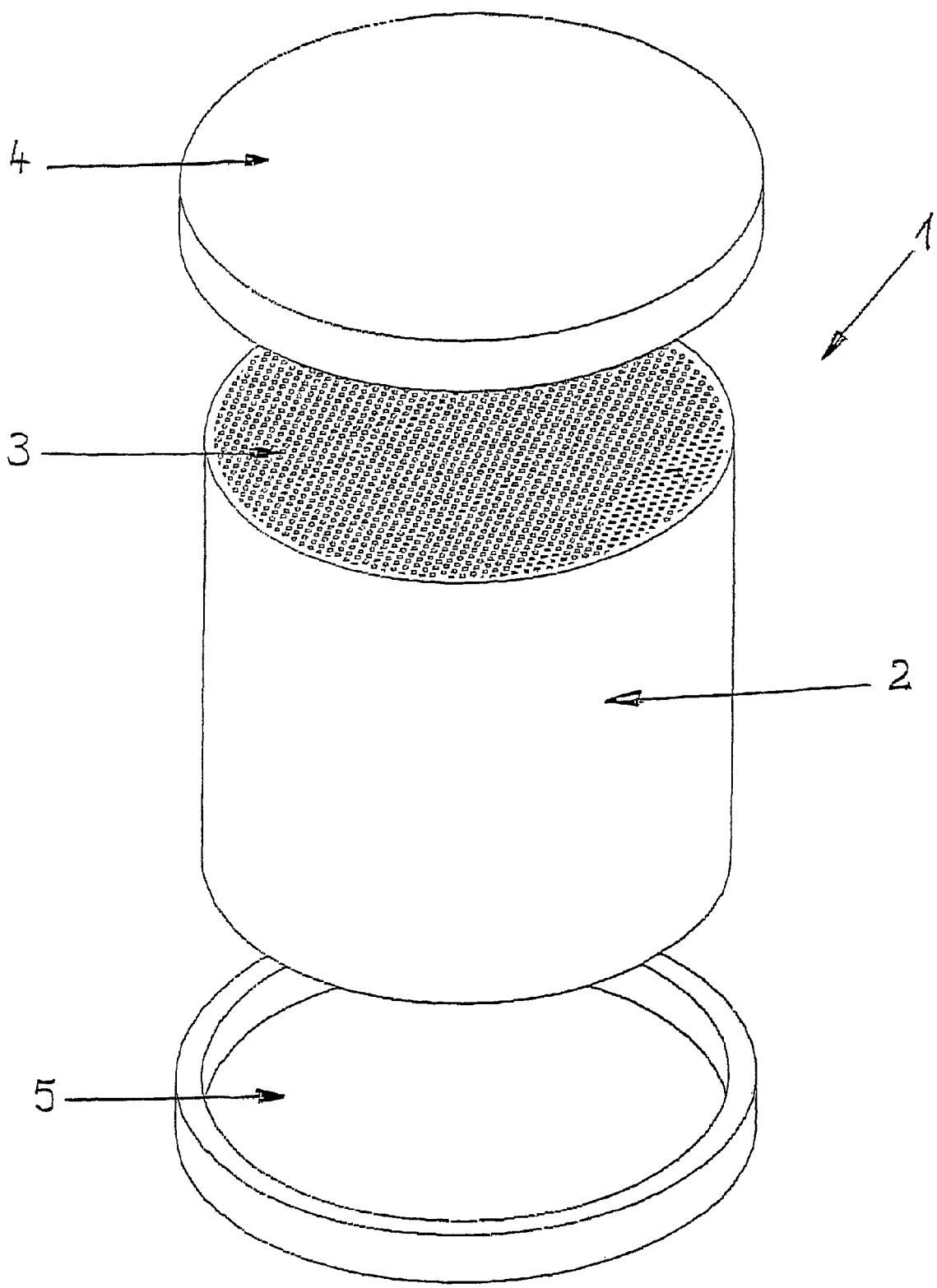

A flow-through or collection container containing a separation element in accordance with the invention is shown in FIG. 3 as an example. The flow-through container 1 that is shown, which is drawn around 5-10 times larger than containers preferably used, has an essentially cylindrical casing 2, a separation element 3 between the supply opening at the bottom and the outlet opening that can be seen at the top, and covers 4 and 5 for closure in a way that is impermeable to toxins. The flow direction for the flowing medium essentially runs parallel to the cylinder axis.

Airborne, especially microbial toxins that are not only significant in cases like the examples above, but also for people in their overall living and working environment, can be detected with the new testing method. Liquids can likewise be tested for contamination with microbial toxins. Biological weapons can also be recognized in this way. Special advantages also lie in the species relevance, the medical relevance, the broad detection spectrum and the possibility to directly test the blood of an affected person in the surroundings relevant to him. The method permits both dead and live material to be recorded on an integral basis in one approach with a flow-through or collection device that can simultaneously be used as an incubation system for measurement. Cell-activating material can analogously be separated out of liquids and enriched if necessary. The sensitivity of the detection reaction can be significantly increased by enriching such contaminations. In addition, interfering components can thus be separated out.

The invention claimed is:

1. A method for testing gas samples or liquid samples for immune-stimulating microbiological substances comprising a) providing a flow through container having a supply opening and an outlet opening, each supply opening and outlet opening having a cover impermeable to microbial substances when closed, and having a separation element or elements inside the flow through container, the separation element or elements comprising filter or filters, b) passing the gas sample or the liquid sample through the supply opening of the flow through container and through the separation element or elements wherein immune-stimulating microbiological substances, if present, in the sample are retained within the filter or filters and wherein the sample exits the container through the outlet opening; c) adding whole blood containing anticoagulants to the surface of separation element or elements thereby contacting the whole blood to the immune-stimulating microbiological substances if present and incubating the filter or filters in the flow through container; d) assaying the whole blood to determine the presence of mediators produced by the whole blood in response to the immune-stimulating microbiological substances if present.

2. A method in accordance with claim 1, which further comprises a quantitative determination of microbiological substances contaminating the respective test medium.

3. A method in accordance with claim 1, wherein the separation element contains filter paper or filter fleeces containing organic fibers or porous ion-exchange resins.

4. A method in accordance with claim 1, wherein the separation element contains cellulose, cellulose ester, polytetrafluoroethylene, polycarbonate and/or glass fibers.

5. A method in accordance with claim 1, wherein the separation elements have toxin-reactive groups.

6. A method in accordance with claim 1, wherein the gas is air.

7. A method in accordance with claim 1, wherein the separation element or elements is arranged in an area between the supply opening and the outlet opening and perpendicularly to the flow of the sample.

8. A method in accordance with claim 1, wherein the liquid is an aqueous or biological preparation.

9. A method in accordance with claim 8, wherein the aqueous or biological preparation is a dialysis liquid.

* * * * *